United States Patent
Houser et al.

(10) Patent No.: US 9,381,058 B2
(45) Date of Patent: Jul. 5, 2016

(54) RECHARGE SYSTEM FOR MEDICAL DEVICES

(75) Inventors: Kevin L. Houser, Cincinnati, OH (US); Gavin M. Monson, Oxford, OH (US); Foster B. Stulen, Mason, OH (US); Daniel W. Price, Loveland, OH (US); Ashvani K. Madan, Mason, OH (US); John W. Willis, Cincinnati, OH (US); Donna L. Korvick, Maineville, OH (US); Aron O. Zingman, Cambridge, MA (US); David C. Yates, West Chester, OH (US); Timothy G. Dietz, Terrace Park, OH (US); Frederick E. Shelton, IV, Hillsboro, OH (US); Jerome R. Morgan, Cincinnati, OH (US); Jeffrey L. Aldridge, Lebanon, OH (US); Bret W. Smith, Kings Mills, OH (US); Hitesh Jain, Rajasthan (IN)

(73) Assignee: Ethicon Endo-Surgery, LLC, Los Frailes Industrial Park Guaynabo, PR (US)

(*) Notice: Subject to any disclaimer, the term of this patent is extended or adjusted under 35 U.S.C. 154(b) by 482 days.

(21) Appl. No.: 13/275,514

(22) Filed: Oct. 18, 2011

(65) Prior Publication Data

US 2012/0112687 A1   May 10, 2012

Related U.S. Application Data

(60) Provisional application No. 61/410,603, filed on Nov. 5, 2010, provisional application No. 61/487,846, filed on May 19, 2011.

(51) Int. Cl.
*H01M 10/46* (2006.01)
*A61B 18/14* (2006.01)
(Continued)

(52) U.S. Cl.
CPC ....... *A61B 18/1442* (2013.01); *A61B 17/00234* (2013.01); *A61B 17/320068* (2013.01);
(Continued)

(58) Field of Classification Search
CPC ..... H02J 7/0013; H02J 7/0042; H02J 7/0047; H02J 7/0021
USPC ................ 320/112, 115, 110, 114, 116, 132, 320/DIG. 21
See application file for complete search history.

(56) References Cited

U.S. PATENT DOCUMENTS

| 1,754,806 A | 4/1930 | Stevenson |
| 3,297,192 A | 1/1967 | Swett |
| 3,419,198 A | 12/1968 | Pettersen |
| 3,619,671 A | 11/1971 | Shoh |
| 4,034,762 A | 7/1977 | Cosens et al. |

(Continued)

FOREIGN PATENT DOCUMENTS

| DE | 102008051866 | 10/2010 |
| DE | 102009013034 | 10/2010 |

(Continued)

OTHER PUBLICATIONS

US Office Action, Notice of Allowance, dated Nov. 21, 2014 for U.S. Appl. No. 13/151,471.

(Continued)

*Primary Examiner* — Edward Tso

(57) ABSTRACT

An apparatus comprises a base and at least one indicator in communication with the base. The base comprises a housing and at least one slot. The at least one slot is shaped to receive a reusable component from a surgical instrument. The at least one indicator is in communication with the at least one slot. The base is configured to detect at least one characteristic related to the reusable component when the reusable component is placed into the at least one slot. Wherein the at least one indicator is configured to provide a signal to the user regarding the at least one characteristic.

19 Claims, 8 Drawing Sheets

(51) Int. Cl.

| | | |
|---|---|---|
| *A61B 17/00* | (2006.01) | |
| *A61B 17/32* | (2006.01) | |
| *A61B 18/00* | (2006.01) | |
| *A61B 18/04* | (2006.01) | |
| *H02J 7/00* | (2006.01) | |
| H01M 2/26 | (2006.01) | |
| H01M 2/10 | (2006.01) | |
| A61B 18/12 | (2006.01) | |
| A61B 19/00 | (2006.01) | |
| A61B 17/064 | (2006.01) | |
| A61B 17/285 | (2006.01) | |
| A61B 17/29 | (2006.01) | |
| A61B 17/28 | (2006.01) | |

(52) U.S. Cl.
CPC ......... *A61B17/320092* (2013.01); *A61B 18/00* (2013.01); *A61B 18/04* (2013.01); *A61B 18/12* (2013.01); *A61B 18/14* (2013.01); *A61B 18/1445* (2013.01); *H02J 7/0045* (2013.01); A61B 17/064 (2013.01); A61B 17/285 (2013.01); A61B 17/2812 (2013.01); A61B 18/1206 (2013.01); A61B 18/1233 (2013.01); A61B 19/38 (2013.01); A61B 19/56 (2013.01); A61B 2017/0046 (2013.01); A61B 2017/00084 (2013.01); A61B 2017/00398 (2013.01); A61B 2017/00473 (2013.01); A61B 2017/00477 (2013.01); A61B 2017/00482 (2013.01); A61B 2017/00734 (2013.01); A61B 2017/291 (2013.01); A61B 2017/293 (2013.01); A61B 2017/294 (2013.01); A61B 2017/2929 (2013.01); A61B 2017/2931 (2013.01); A61B 2017/2933 (2013.01); A61B 2018/0019 (2013.01); A61B 2018/00178 (2013.01); A61B 2018/00791 (2013.01); A61B 2018/00988 (2013.01); A61B 2018/1226 (2013.01); A61B 2018/1412 (2013.01); A61B 2018/1455 (2013.01); A61B 2019/4815 (2013.01); A61B 2019/4868 (2013.01); A61B 2019/4873 (2013.01); H01M 2/10 (2013.01); H01M 2/26 (2013.01); Y10T 29/49005 (2015.01); Y10T 29/49895 (2015.01); Y10T 29/53913 (2015.01)

(56) References Cited

U.S. PATENT DOCUMENTS

| | | | |
|---|---|---|---|
| 4,057,220 A | 11/1977 | Kudlacek | |
| 4,535,773 A | 8/1985 | Yoon | |
| 4,641,076 A | 2/1987 | Linden et al. | |
| 4,641,077 A | 2/1987 | Pascaloff | |
| 4,662,068 A | 5/1987 | Polonsky | |
| 4,666,037 A | 5/1987 | Weissman | |
| 4,685,459 A | 8/1987 | Koch et al. | |
| 4,717,018 A | 1/1988 | Sacherer et al. | |
| 4,717,050 A | 1/1988 | Wright | |
| 4,721,097 A | 1/1988 | D'Amelio | |
| 4,768,969 A | 9/1988 | Bauer et al. | |
| 4,800,878 A | 1/1989 | Cartmell | |
| 4,844,259 A | 7/1989 | Glowczewskie, Jr. et al. | |
| 4,878,493 A | 11/1989 | Pasternak et al. | |
| 5,071,417 A | 12/1991 | Sinofsky | |
| 5,107,155 A | 4/1992 | Yamaguchi | |
| 5,144,771 A | 9/1992 | Miwa | |
| 5,169,733 A | 12/1992 | Savovic et al. | |
| 5,176,677 A | 1/1993 | Wuchinich | |
| 5,246,109 A | 9/1993 | Markle et al. | |
| 5,273,177 A | 12/1993 | Campbell | |
| 5,277,694 A | 1/1994 | Leysieffer et al. | |
| 5,308,358 A | 5/1994 | Bond et al. | |
| 5,322,055 A | 6/1994 | Davison et al. | |
| 5,339,799 A | 8/1994 | Kami et al. | |
| 5,358,508 A | 10/1994 | Cobb et al. | |
| 5,361,902 A | 11/1994 | Abidin et al. | |
| 5,429,229 A | 7/1995 | Chester et al. | |
| 5,449,370 A | 9/1995 | Vaitekunas | |
| 5,454,378 A | 10/1995 | Palmer et al. | |
| 5,501,607 A | 3/1996 | Yoshioka et al. | |
| 5,507,297 A | 4/1996 | Slater et al. | |
| 5,561,881 A | 10/1996 | Klinger et al. | |
| 5,578,052 A | 11/1996 | Koros et al. | |
| 5,580,258 A | 12/1996 | Wakata | |
| 5,582,617 A | 12/1996 | Klieman et al. | |
| 5,590,778 A | 1/1997 | Dutchik | |
| 5,592,065 A * | 1/1997 | Oglesbee et al. | 320/113 |
| 5,597,531 A | 1/1997 | Liberti et al. | |
| 5,599,350 A | 2/1997 | Schulze et al. | |
| 5,630,420 A | 5/1997 | Vaitekunas | |
| 5,630,456 A | 5/1997 | Hugo et al. | |
| 5,690,222 A | 11/1997 | Peters | |
| 5,707,369 A | 1/1998 | Vaitekunas et al. | |
| 5,741,305 A | 4/1998 | Vincent et al. | |
| 5,776,155 A | 7/1998 | Beaupre et al. | |
| 5,800,336 A | 9/1998 | Ball et al. | |
| 5,817,128 A | 10/1998 | Storz | |
| 5,868,244 A | 2/1999 | Ivanov et al. | |
| 5,873,873 A | 2/1999 | Smith et al. | |
| 5,882,310 A | 3/1999 | Marian, Jr. | |
| 5,935,144 A | 8/1999 | Estabrook | |
| 5,938,633 A | 8/1999 | Beaupre | |
| 5,944,737 A | 8/1999 | Tsonton et al. | |
| 5,951,575 A | 9/1999 | Bolduc et al. | |
| 5,980,510 A | 11/1999 | Tsonton et al. | |
| 5,997,531 A | 12/1999 | Loeb et al. | |
| 6,018,227 A | 1/2000 | Kumar et al. | |
| 6,051,010 A | 4/2000 | DiMatteo et al. | |
| 6,056,735 A | 5/2000 | Okada et al. | |
| 6,063,098 A | 5/2000 | Houser et al. | |
| 6,066,151 A | 5/2000 | Miyawaki et al. | |
| 6,083,191 A | 7/2000 | Rose | |
| 6,083,223 A | 7/2000 | Baker | |
| 6,099,537 A | 8/2000 | Sugai et al. | |
| 6,113,593 A | 9/2000 | Tu et al. | |
| 6,123,702 A | 9/2000 | Swanson et al. | |
| 6,165,191 A | 12/2000 | Shibata et al. | |
| 6,204,592 B1 | 3/2001 | Hur | |
| 6,214,023 B1 | 4/2001 | Whipple et al. | |
| 6,246,896 B1 | 6/2001 | Dumoulin et al. | |
| 6,248,238 B1 | 6/2001 | Burtin et al. | |
| 6,287,304 B1 | 9/2001 | Eggers et al. | |
| 6,325,811 B1 | 12/2001 | Messerly | |
| 6,339,368 B1 | 1/2002 | Leith | |
| 6,398,755 B1 | 6/2002 | Belef et al. | |
| 6,409,742 B1 | 6/2002 | Fulton, III et al. | |
| 6,500,176 B1 | 12/2002 | Truckai et al. | |
| 6,500,188 B2 | 12/2002 | Harper et al. | |
| 6,512,667 B2 | 1/2003 | Shiue et al. | |
| 6,514,267 B2 | 2/2003 | Jewett | |
| 6,520,185 B1 | 2/2003 | Bommannan et al. | |
| 6,561,983 B2 | 5/2003 | Cronin et al. | |
| 6,562,032 B1 | 5/2003 | Ellman et al. | |
| 6,609,414 B2 | 8/2003 | Mayer et al. | |
| 6,622,731 B2 | 9/2003 | Daniel et al. | |
| 6,623,500 B1 | 9/2003 | Cook et al. | |
| 6,626,901 B1 | 9/2003 | Treat et al. | |
| 6,647,281 B2 | 11/2003 | Morency | |
| 6,650,091 B1 | 11/2003 | Shiue et al. | |
| 6,650,975 B2 | 11/2003 | Ruffner | |
| 6,656,177 B2 | 12/2003 | Truckai et al. | |
| 6,658,301 B2 | 12/2003 | Loeb et al. | |
| 6,666,875 B1 * | 12/2003 | Sakurai et al. | 606/169 |
| 6,706,038 B2 | 3/2004 | Francischelli et al. | |
| 6,717,193 B2 | 4/2004 | Olewine et al. | |
| 6,730,042 B2 | 5/2004 | Fulton et al. | |
| 6,753,673 B2 | 6/2004 | Shiue et al. | |
| 6,758,855 B2 | 7/2004 | Fulton, III et al. | |
| 6,761,698 B2 | 7/2004 | Shibata et al. | |
| 6,761,701 B2 | 7/2004 | Cucin | |
| 6,783,524 B2 | 8/2004 | Anderson et al. | |
| 6,815,206 B2 | 11/2004 | Lin et al. | |

(56) References Cited

U.S. PATENT DOCUMENTS

| | | |
|---|---|---|
| 6,821,671 B2 | 11/2004 | Hinton et al. |
| 6,836,097 B2 | 12/2004 | Turner et al. |
| 6,838,862 B2 | 1/2005 | Luu |
| 6,847,192 B2 | 1/2005 | Turner et al. |
| 6,860,880 B2 | 3/2005 | Treat et al. |
| 6,869,435 B2 | 3/2005 | Blake |
| 6,923,807 B2 | 8/2005 | Ryan et al. |
| 6,982,696 B1 | 1/2006 | Shahoian |
| 6,998,822 B2 | 2/2006 | Turner et al. |
| 7,031,155 B2 | 4/2006 | Sauciuc et al. |
| 7,061,749 B2 | 6/2006 | Liu et al. |
| 7,077,853 B2 | 7/2006 | Kramer et al. |
| 7,083,589 B2 | 8/2006 | Banko et al. |
| 7,085,123 B2 | 8/2006 | Shiue et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,186,473 B2 | 3/2007 | Shiue et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,353,068 B2 | 4/2008 | Tanaka et al. |
| 7,354,440 B2 | 4/2008 | Truckai et al. |
| 7,364,061 B2 | 4/2008 | Swayze et al. |
| 7,364,554 B2 | 4/2008 | Bolze et al. |
| 7,375,644 B2 | 5/2008 | Miyazawa |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,560,903 B2 | 7/2009 | Thrap |
| 7,563,142 B1 | 7/2009 | Wenger et al. |
| 7,573,151 B2 | 8/2009 | Acena et al. |
| 7,583,564 B2 | 9/2009 | Ketahara et al. |
| 7,638,958 B2 | 12/2009 | Philipp et al. |
| 7,643,378 B2 | 1/2010 | Genosar |
| 7,658,247 B2 | 2/2010 | Carter |
| 7,692,411 B2 | 4/2010 | Trainor et al. |
| 7,717,312 B2 | 5/2010 | Beetel |
| 7,721,936 B2 | 5/2010 | Shalton, IV et al. |
| 7,738,971 B2 | 6/2010 | Swayze et al. |
| 7,761,198 B2 | 7/2010 | Bhardwaj |
| 7,766,910 B2 | 8/2010 | Hixson et al. |
| 7,766,929 B2 | 8/2010 | Masuda |
| 7,770,722 B2 | 8/2010 | Donahoe et al. |
| 7,770,775 B2 | 8/2010 | Shelton et al. |
| 7,776,037 B2 | 8/2010 | Odom |
| 7,780,660 B2 | 8/2010 | Bourne et al. |
| 7,802,121 B1 | 9/2010 | Zansky et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,889,489 B2 | 2/2011 | Richardson et al. |
| 7,922,063 B2 | 4/2011 | Zemlok et al. |
| 7,923,151 B2 | 4/2011 | Lam et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 7,977,921 B2 | 7/2011 | Bahai et al. |
| 7,982,439 B2 | 7/2011 | Trainor et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,097,011 B2 | 1/2012 | Sanai et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,642 B2 | 8/2012 | Houser et al. |
| 8,251,994 B2 | 8/2012 | McKenna et al. |
| 8,267,094 B2 | 9/2012 | Danek et al. |
| 8,277,446 B2 | 10/2012 | Heard |
| 8,292,888 B2 | 10/2012 | Whitman |
| 8,298,253 B2 | 10/2012 | Charles |
| 8,323,271 B2 | 12/2012 | Humayun et al. |
| 8,336,725 B2 | 12/2012 | Ramsey et al. |
| 8,344,690 B2 * | 1/2013 | Smith et al. .................. 320/108 |
| 8,377,059 B2 | 2/2013 | Deville et al. |
| 8,400,108 B2 | 3/2013 | Powell et al. |
| 8,419,758 B2 | 4/2013 | Smith et al. |
| 8,425,545 B2 | 4/2013 | Smith et al. |
| 8,444,653 B2 | 5/2013 | Nycz et al. |
| 8,449,529 B2 | 5/2013 | Bek et al. |
| 8,459,520 B2 | 6/2013 | Giordano et al. |
| 8,487,487 B2 | 7/2013 | Dietz et al. |
| 8,522,795 B2 * | 9/2013 | Bouix et al. .................. 320/114 |
| 8,564,242 B2 * | 10/2013 | Hansford et al. ............. 320/107 |
| 8,573,461 B2 | 11/2013 | Shelton et al. |
| 8,617,077 B2 | 12/2013 | van Groningen et al. |
| 8,636,736 B2 | 1/2014 | Yates et al. |
| 8,663,112 B2 | 3/2014 | Slayton et al. |
| 9,044,261 B2 | 6/2015 | Houser |
| 2001/0032666 A1 | 10/2001 | Jenson et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2003/0144680 A1 | 7/2003 | Kellogg et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2004/0212344 A1 * | 10/2004 | Tamura et al. ................. 320/114 |
| 2005/0021065 A1 | 1/2005 | Yamada et al. |
| 2005/0033195 A1 | 2/2005 | Fulton et al. |
| 2005/0171522 A1 | 8/2005 | Christopherson |
| 2005/0203546 A1 | 9/2005 | Van Wyk et al. |
| 2005/0256522 A1 | 11/2005 | Francischelli et al. |
| 2006/0030797 A1 | 2/2006 | Zhou et al. |
| 2006/0079829 A1 | 4/2006 | Fulton et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0084742 A1 | 4/2007 | Miller et al. |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0161783 A1 | 7/2008 | Cao |
| 2008/0173651 A1 | 7/2008 | Ping |
| 2008/0188810 A1 | 8/2008 | Larsen et al. |

(56) References Cited

U.S. PATENT DOCUMENTS

| | | |
|---|---|---|
| 2008/0200940 A1 | 8/2008 | Eichmann et al. |
| 2008/0221491 A1 | 9/2008 | Slayton et al. |
| 2008/0228104 A1 | 9/2008 | Uber, III et al. |
| 2008/0255413 A1 | 10/2008 | Zemlok et al. |
| 2008/0281301 A1 | 11/2008 | DeBoer et al. |
| 2008/0315829 A1 | 12/2008 | Jones et al. |
| 2009/0030437 A1 | 1/2009 | Houser et al. |
| 2009/0033276 A1* | 2/2009 | Ishii .............. 320/103 |
| 2009/0043797 A1 | 2/2009 | Dorie et al. |
| 2009/0076506 A1 | 3/2009 | Baker |
| 2009/0096430 A1 | 4/2009 | Van Der Linde et al. |
| 2009/0105750 A1 | 4/2009 | Price et al. |
| 2009/0112099 A1* | 4/2009 | Kurokawa .............. 600/459 |
| 2009/0125026 A1 | 5/2009 | Rioux et al. |
| 2009/0137952 A1 | 5/2009 | Ramamurthy et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0198307 A1* | 8/2009 | Mi et al. ............. 607/60 |
| 2009/0209979 A1 | 8/2009 | Yates et al. |
| 2009/0209990 A1 | 8/2009 | Yates et al. |
| 2009/0240246 A1 | 9/2009 | Deville et al. |
| 2009/0253030 A1* | 10/2009 | Kooij ............. 429/100 |
| 2009/0264940 A1 | 10/2009 | Beale et al. |
| 2009/0275940 A1 | 11/2009 | Malackowski et al. |
| 2009/0281430 A1 | 11/2009 | Wilder |
| 2009/0281464 A1 | 11/2009 | Cioanta et al. |
| 2010/0016855 A1 | 1/2010 | Ramstein et al. |
| 2010/0021022 A1 | 1/2010 | Pittel et al. |
| 2010/0030218 A1 | 2/2010 | Prevost |
| 2010/0039071 A1* | 2/2010 | Hansford et al. ............. 320/162 |
| 2010/0060231 A1 | 3/2010 | Trainor et al. |
| 2010/0069940 A1 | 3/2010 | Miller et al. |
| 2010/0076455 A1 | 3/2010 | Birkenbach et al. |
| 2010/0089970 A1 | 4/2010 | Smith et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Lyell Kirby et al. |
| 2010/0211053 A1 | 8/2010 | Ross et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2010/0301095 A1 | 12/2010 | Shelton, IV et al. |
| 2011/0009694 A1 | 1/2011 | Schultz et al. |
| 2011/0015660 A1 | 1/2011 | Wiener et al. |
| 2011/0058982 A1 | 3/2011 | Kaneko |
| 2011/0074336 A1 | 3/2011 | Miller |
| 2011/0077514 A1 | 3/2011 | Ulric et al. |
| 2011/0080134 A1 | 4/2011 | Miller |
| 2011/0087212 A1 | 4/2011 | Aldridge et al. |
| 2011/0087218 A1 | 4/2011 | Boudreaux et al. |
| 2011/0152901 A1 | 6/2011 | Woodruff et al. |
| 2011/0221398 A1 | 9/2011 | Ferber |
| 2011/0224668 A1 | 9/2011 | Johnson et al. |
| 2011/0247952 A1 | 10/2011 | Hebach et al. |
| 2011/0288573 A1 | 11/2011 | Yates et al. |
| 2012/0179036 A1 | 7/2012 | Patrick et al. |
| 2012/0265230 A1 | 10/2012 | Laurent et al. |
| 2012/0283732 A1 | 11/2012 | Lam |
| 2012/0292367 A1 | 11/2012 | Morgan et al. |
| 2013/0085330 A1 | 4/2013 | Ramamurthy et al. |
| 2013/0085332 A1 | 4/2013 | Ramamurthy et al. |
| 2013/0085397 A1 | 4/2013 | Ramamurthy et al. |
| 2013/0090528 A1 | 4/2013 | Ramamurthy et al. |
| 2013/0090530 A1 | 4/2013 | Ramamurthy et al. |
| 2013/0090552 A1 | 4/2013 | Ramamurthy et al. |
| 2013/0116690 A1 | 5/2013 | Unger et al. |
| 2013/0118733 A1 | 5/2013 | Kumar |
| 2013/0342962 A1 | 12/2013 | Fletcher et al. |
| 2014/0088739 A1 | 3/2014 | Ellis et al. |
| 2015/0305763 A1 | 10/2015 | Houser et al. |

FOREIGN PATENT DOCUMENTS

| | | |
|---|---|---|
| EP | 0947167 A1 | 1/1999 |
| EP | 0897696 A1 | 2/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| JP | 2010-518978 | 6/2010 |
| JP | 5410110 B | 2/2014 |
| WO | WO 97/24072 | 7/1997 |
| WO | WO 00/65682 | 2/2000 |
| WO | WO 03/013374 | 2/2003 |
| WO | WO 03/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/050439 | 5/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

US Office Action, Notice of Allowance, dated Nov. 21, 2014 for U.S. Appl. No. 13/151,498.

US Office Action, Notice of Allowance, dated Dec. 17, 2014 for U.S. Appl. No. 13/270,667.

US Office Action, Non-Final, dated Dec. 16, 2014 for U.S. Appl. No. 13/270,701.

US Office Action, Notice of Allowance, dated Nov. 28, 2014 for U.S. Appl. No. 13/274,805.

US Office Action, Notice of Allowance, dated Dec. 19, 2014 for U.S. Appl. No. 13/276,745.

US Office Action, Non-Final, dated Dec. 8, 2014 for U.S. Appl. No. 13/277,328.

Notice of Allowance dated Dec. 6, 2013 for U.S. Appl. No. 13/151,471.

Office Action Final dated Nov. 21, 2013 for U.S. Appl. No. 13/151,498.

(56) References Cited

OTHER PUBLICATIONS

Office Action Non-Final dated Sep. 26, 2013 for U.S. Appl. No. 13/151,509.
Office Action Final dated Oct. 25, 2013 for U.S. Appl. No. 13/270,667.
Office Action Non-Final dated Nov. 21, 2013 for U.S. Appl. No. 13/271,352.
Restriction Requirement dated Dec. 9, 2013 for U.S. Appl. No. 13/274,496.
Office Action Non-Final dated Dec. 6, 2013 for Appli No. 13/274,516.
Office Action Final dated Oct. 25, 2013 for U.S. Appl. No. 13/274,540.
Office Action Final dated Nov. 26, 2013 for U.S. Appl. No. 13/274,830.
Office Action Final dated Dec. 5, 2013 for U.S. Appl. No. 13/275,495.
Notice of Allowance dated Nov. 12, 2013 for U.S. Appl. No. 13/276,687.
Office Action Final dated Sep. 27, 2013 for U.S. Appl. No.13/276,707.
Office Action Final dated Nov. 8, 2013 for U.S. Appl. No. 13/276,745.
European Communication dated Feb. 19, 2014 for Application No. EP 11781972.2.
International Preliminary Report on Patentability for Application No. PCT/US2011/059212 dated May 7, 2013.
International Preliminary Report on Patentability for Application No. PCT/US2011/059215 dated May 8, 2013.
International Preliminary Report on Patentability for Application No. PCT/US2011/059217 dated May 7, 2013.
International Preliminary Report on Patentability for Application No. PCT/US2011/059218 dated May 7, 2013.
International Preliminary Report on Patentability for Application No. PCT/US2011/059220 dated May 7, 2013.
International Preliminary Report on Patentability for Application No. PCT/US2011/059222 dated May 7, 2013.
International Preliminary Report on Patentability for Application No. PCT/US2011/059223 dated May 7, 2013.
International Preliminary Report on Patentability for Application No. PCT/US2011/059226 dated May 7, 2013.
International Preliminary Report on Patentability for Application No. PCT/US2011/059338 dated May 7, 2013.
International Preliminary Report on Patentability for Application No. PCT/US2011/059351 dated May 7, 2013.
International Preliminary Report on Patentability for Application No. PCT/US2011/059354 dated May 7, 2013.
International Preliminary Report on Patentability for Application No. PCT/US2011/059358 dated May 7, 2013.
International Preliminary Report on Patentability for Application No. PCT/US2011/059362 dated May 7, 2013.
International Preliminary Report on Patentability for Application No. PCT/US2011/059365 dated May 8, 2013.
International Preliminary Report on Patentability for Application No. PCT/US2011/059371 dated May 7, 2013.
International Preliminary Report on Patentability for Application No. PCT/US2011/059378 dated May 7, 2013.
International Preliminary Report on Patentability for Application No. PCT/US2011/059381 dated May 8, 2013.
Office Action Non-Final dated Mar. 28, 2014 for U.S. Appl. No. 13/151,471.
Office Action Non Final dated Mar. 18, 2014 for U.S. Appl. No. 13/151,498.
Office Action Non Final dated Jun. 18, 2014 for U.S. Appl. No. 13/151,503.
Office Action Final dated Jan. 29, 2014 for U.S. Appl. No. 13/151,509.
Restriction Requirement dated Jun. 11, 2014 for U.S. Appl. No. 13/151,512.
Office Action Non-Final dated Feb. 14, 2014 for U.S. Appl. No. 13/274,480.
Office Action Non-Final dated Feb. 6, 2014 for U.S. Appl. No. 13/274,496.
Office Action Final dated May 15, 2014 for U.S. Appl. No. 13/274,496 1.
Restriction Requirement dated Mar. 28, 2014 for U.S. Appl. No. 13/274,507.
Office Action Non-Final dated Jun. 19, 2014 for U.S. Appl. No. 13/274,507.
Office Action Final dated Jun. 12, 2014 for U.S. Appl. No. 13/274,516.
Office Action Final dated Feb. 28, 2014 for U.S. Appl. No. 13/275,547.
Office Action Final dated Mar. 21, 2014 for U.S. Appl. No. 13/276,673.
Notice of Allowance dated Jun. 2, 2014 for U.S. Appl. No. 13/276,687.
Office Action Non-Final dated Feb. 28, 2014 for U.S. Appl. No. 13/276,745.
US Office Action, Notice of Allowance, dated Aug. 19, 2014 for U.S. Appl. No. 13/151,471.
1 US Office Action, Non-Final, dated Aug. 14, 2014 for U.S. Appl. No. 13/151,481.
US Office Action, Non-Final, dated Nov. 7, 2014 for U.S. Appl. No. 13/151,488.
US Office Action, Notice of Allowance, dated Aug. 6, 2014 for U.S. Appl. No. 13/151,498.
Office Action, Notice of Allowance, dated Nov. 21, 2014 for U.S. Appl. No. 13/151,498.
US Office Action, Non-Final, dated Nov. 6, 2014 for U.S. Appl. No. 13/151,503.
US Office Action, Non-Final, dated Jul. 9, 2014 for U.S. Appl. No. 13/151,509.
US Office Action, Notice of Allowance, dated Oct. 28, 2014 for U.S. Appl. No. 13/151,509.
US Office Action, Notice of Allowance, dated Oct. 29, 2014 for U.S. Appl. No. 13/151,512.
US Office Action, Restriction Requirement, dated Jul. 11, 2014 for U.S. Appl. No. 13/269,870.
US Office Action, Non-Final, dated Jul. 29, 2014 for U.S. Appl. No. 13/270,667.
US Office Action, Restriction Requirement, dated Jul. 9, 2014 for U.S. Appl. No. 13/270,684.
US Office Action, Non-Final, dated Oct. 9, 2014 for U.S. Appl. No. 13/270,684.
US Office Action, Restriction Requirement, dated Sep. 11, 2014 for U.S. Appl. No. 13/270,701.
US Office Action, Restriction Requirement, dated Sep. 25, 2014 for U.S. Appl. No. 13/271,352.
US Office Action, Restriction Requirement, dated Oct. 2, 2013 for U.S. Appl. No. 13/274,480.
US Office Action, Final, dated Jul. 17, 2014 for U.S. Appl. No. 13/274,480.
US Office Action, Final, dated Aug. 22, 2014 for U.S. Appl. No. 13/274,496.
US Office Action, Non-Final, dated Oct. 8, 2014 for U.S. Appl. No. 13/274,516.
US Office Action, Non-Final, dated Aug. 26, 2014 for U.S. Appl. No. 13/274,540.
US Office Action, Non-Final, dated Aug. 14, 2014 for U.S. Appl. No. 13/274,805.
US Office Action, Notice of Allowance, dated Nov. 24, 2014 for U.S. Appl. No. 13/274,805.
US Office Action, Non-Final, dated Oct. 22, 2014 for U.S. Appl. No. 13/274,830.
US Office Action, Non-Final, dated Aug. 20, 2014 for U.S. Appl. No. 13/275,547.
Action, Non-Final, dated Oct. 23, 2014 for U.S. Appl. No. 13/275,563.
US Office Action, Restriction Requirement, dated Jul. 9, 2014 for U.S. Appl. No. 13/276,660.

(56) References Cited

OTHER PUBLICATIONS

US Office Action, Non-Final, dated Aug. 14, 2014 for U.S. Appl. No. 13/276,673.
US Office Action, Notice of Allowance, dated Sep. 12, 2014 for U.S. Appl. No. 13/276,687.
US Office Action, Non-Final, dated Aug. 20, 2014 for U.S. Appl. No. 13/276,725.
US Office Action, Notice of Allowance, dated Oct. 7, 2014 for U.S. Appl. No. 13/276,745.
US Office Action, Restriction Requirement, dated Sep. 24, 2014 for U.S. Appl. No. 13/277,328.
International Search Report and Written Opinion dated Jul. 6, 2012 for PCT/US2011/059381.
Office Action Non-Final dated Aug. 6, 2013 for U.S. Appl. No. 13/151,471.
Restriction Requirement date Jul. 5, 2013 for U.S. Appl. No. 13/151,488.
Office Action Non-Final dated Jul. 14, 2013 for U.S. Appl. No. 13/151,498.
Restriction Requirement datef Jun. 24, 2013 for U.S. Appl. No. 13/151,509.
Office Action Final dated Aug. 16, 2013 for U.S. Appl. No. 13/274,516.
Office Action Final dated Sep. 12, 2013 for U.S. Appl. No. 13/274,805.
Office Action Non-Final dated Jun. 14, 2013 for U.S. Appl. No. 13/274,830.
Office Action Final dated Aug. 29, 2013 for U.S. Appl. No. 13/275,563.
Office Action Non-Final dated Aug. 19, 2013 for U.S. Appl. No. 13/276,673.
Office Action Non-Final dated Jun. 12, 2013 for U.S. Appl. No. 13/276,687.
International Search Report dated Jan. 26, 2012 for Application No. PCT/US11/059220.
International Search Report dated Feb. 1, 2012 for Application No. PCT/US11/059223.
International Search Report dated Jan. 12, 2012 for Application No. PCT/US11/059226.
International Search Report dated May 29, 2012 for Application No. PCT/US11/059358.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
Restriction Requirement dated Mar. 13, 2013 for U.S. Appl. No. 13/151,509.
Restriction Requirement dated Feb. 28, 2013 for U.S. Appl. No. 13/270,667.
Office Action Non-Final dated Apr. 26, 2013 for U.S. Appl. No. 13/270,667.
Office Action Non-Final dated Dec. 21, 2012 for U.S. Appl. No. 13/274,516.
Restriction Requirement dated Feb. 25, 2013 for U.S. Appl. No. 13/274,540.
Office Action Non Final dated Apr. 30, 2013 for U.S. Appl. No. 13/274,540.
Office Action Non Final dated Apr. 1, 2013 for U.S. Appl. No. 13/274,805.
Restriction Requirement dated Apr. 29, 2013 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Non-Final dated May 17, 2013 for U.S. Appl. No. 13/275,547.
Office Action Non-Final dated Feb. 1, 2013 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/246,660.
Office Action Non-Final dated Dec. 21, 2012 for U.S. Appl. No. 13/276,673.
Restriction Requirement dated Feb. 6, 2013 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Restriction Requirement dated Feb. 6, 2013 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
U.S. Appl. No. 13/151,471, filed Jun. 2, 2011, Stulen.
U.S. Appl. No. 13/151,481, filed Jun. 2, 2011, Yates et al.
U.S. Appl. No. 13/151,488, filed Jun. 2, 2011, Shelton, IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,509, filed Jun. 2, 2011, Smith et al.
U.S. Appl. No. 13/151,512, filed Jun. 2, 2011, Houser et al.
U.S. Appl. No. 13/151,515, filed Jun. 2, 2011, Felder et al.
U.S. Appl. No. 13/176,875, filed Jul. 6, 2011, Smith et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux et al.
U.S. Appl. No. 13/270,667, filed Oct. 11, 2011, Timm et al.
U.S. Appl. No. 13/270,684, filed Oct. 11, 2011, Madan et al.
U.S. Appl. No. 13/270,701, filed Oct. 11, 2011, Johnson et al.
U.S. Appl. No. 13/271,352, filed Oct. 12, 2011, Houser et al.
U.S. Appl. No. 13/271,364, filed Oct. 12, 2011, Houser et al.
U.S. Appl. No. 13/274,480, filed Oct. 17, 2011, Mumaw et al.
U.S. Appl. No. 13/274,496, filed Oct. 17, 2011, Houser et al.
U.S. Appl. No. 13/274,507, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madan.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.
U.S. Appl. No. 13/276,707, filed Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.
Dietz, T. et al., Partially Implantable Vibrating Ossicular Prosthesis, Transducers'97, vol. 1, International Conference on Solid State Sensors and Actuators, (Jun. 16-19, 1997)pp. 433-436 (Abstract).
"System 6 Aseptic Battery System," Stryker (2006) pp. 1-2.
International Search Report and Written Opinion dated Jan. 16, 2012 for Application No. PCT/US2011/059212.
International Search Report and Written Opinion dated Feb. 2, 2012 for Application No. PCT/US2011/059378.
International Search Report dated Feb. 2, 2012 for Application No. PCT/US2011/059354.
International Search Report dated Feb. 7, 2012 for Application No. PCT/US2011/059351.
International Search Report dated Feb. 13, 2012 for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012 for Application No. PCT/US2011/059362.

(56) References Cited

OTHER PUBLICATIONS

International Search Report dated Apr. 4, 2012 for Application No. PCT/US2011/059215.
International Search Report dated Apr. 11, 2012 for Application No. PCT/US2011/059381.
International Search Report dated Apr. 18, 2012 for Application No. PCT/US2011/059222.
International Search Report dated May 24, 2012 for Application No. PCT/US2011/059378.
International Search Report dated Jun. 4, 2012 for Application No. PCT/US2011/059365.
International Search Report dated Jun. 12, 2012 for Application No. PCT/US2011/059218.
Communication from International Searching Authority dated Feb. 6, 2012 for Application No. PCT/US2011/059362.
Communication from International Searching Authority dated Feb. 2, 2012 for Application No. PCT/US2011/059222.
Communication from International Searching Authority dated Jan. 24, 2012 for Application No. PCT/US2011/059215.
Communication from International Searching Authority dated Feb. 2, 2012 for Application No. PCT/US2011/059378.
Chinese Office Action dated Jan. 29, 2015 for Application No. 201180064010.6.
Chffiese Office Action dated Feb. 2, 2015 for Application No. 201180053450.1.
Chinese Office Action dated Apr. 20, 2015 for Application No. 201180053434.2.
Chinese Office Action dated Aug. 28, 2015 for Application No. 201180064010.6.
Japanese Office Action, Notification of Reasons for Refusal, dated Sep. 1, 2015 for Application No. 2013-537837.
Japanese Office Action, Notification of Reasons for Refusal, dated Sep. 1, 2015 for Application No. 2013-537866.
Japanese Office Action, Notification of Reasons for Refusal, dated Oct. 6, 2015 for Application No. 2013-537869.
US Office Action, Final, dated Jun. 8, 2015 for U.S. Appl. No. 13/151,503.
US Office Action, Non-Final, dated Oct. 2, 2015 for U.S. Appl. No. 13/151,503.
US Office Action, Non-Final, dated Feb. 25, 2015 for U.S. Appl. No. 13/275,495.
US Office Action, Final, dated May 27, 2015 for U.S. Appl. No. 13/275,495.
US Office Action, Final, dated Mar. 10, 2015 for U.S. Appl. No. 13/275,547.
US Office Action, Non-Final, dated Aug. 28, 2015 for U.S. Appl. No. 13/275,547.

\* cited by examiner

RECHARGE SYSTEM FOR MEDICAL DEVICES

PRIORITY

This application claims priority to U.S. Provisional Application Ser. No. 61/410,603, filed Nov. 5, 2010, entitled "Energy-Based Surgical Instruments," the disclosure of which is incorporated by reference herein. This application also claims priority to U.S. Provisional Application Ser. No. 61/487,846, filed May 19, 2011, entitled "Energy-Based Surgical Instruments," the disclosure of which is incorporated by reference herein.

BACKGROUND

With the advancement of the electronics industry, many medical devices that rely on some form of electric power may be adapted to contain most, if not all, of the required components within the medical device. More specifically, some medical devices may be adapted to use an internal or attachable power source instead of requiring the device to be plugged into an external power source by a cable. Merely exemplary devices that may be adapted to include a portable power source are disclosed in U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; U.S. Pub. No. 2006/0079874 entitled "Tissue Pad for Use with an Ultrasonic Surgical Instrument," published Apr. 13, 2006, now abandoned, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, now abandoned, the disclosure of which is incorporated by reference herein; U.S. Pub. No. 2008/0200940 entitled "Ultrasonic Device for Cutting and Coagulating," published Aug. 21, 2008, now abandoned, the disclosure of which is incorporated by reference herein; U.S. Pat. Pub. No. 2009/0143797, entitled "Cordless Hand-held Ultrasonic Cautery Cutting Device," published Jun. 4, 2009, issued as U.S. Pat. No. 8,419,757 on Apr. 16, 2013, the disclosure of which is incorporated by reference herein; U.S. Pub. No. 2009/0209990 entitled "Motorized Surgical Cutting and Fastening Instrument Having Handle Based Power Source," published Aug. 20, 2009, issued as U.S. Pat. No. 8,657,174 on Feb. 25, 2014, the disclosure of which is incorporated by reference herein; U.S. Pub. No. 2010/0069940 entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein. Similarly, various ways in which medical devices may be adapted to include a portable power source are disclosed in U.S. Provisional Application Ser. No. 61/410,603, filed Nov. 5, 2010, entitled "Energy-Based Surgical Instruments," now expired, the disclosure of which is incorporated by reference herein.

Additional exemplary devices that may be adapted to include a portable power source are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; and U.S. patent application Ser. No. 13/151,481, entitled "Motor Driven Electrosurgical Device with Mechanical and Electrical Feedback," filed Jun. 2, 2011, published as U.S. Pub. No. 2012/0116379 on May 10, 2012, now U.S. Pat. No. 9,161,803, issued Oct. 20, 2015, the disclosure of which is incorporated by reference herein.

Electrically powered medical devices such as those referred to herein may require an internal or otherwise integral power source (e.g., a battery or battery pack, etc.) to be charged or recharged immediately before use, during use, or otherwise. In some settings (e.g., those where a charging device is re-used several times, etc.), it may be desirable to provide some degree of isolation between a charging device and the medical device to thereby reduce the likelihood that the charging device will contaminate the medical device and/or to reduce the likelihood that the medical device will contaminate the charging device. Similarly, it may be desirable to facilitate charging or recharging of the power source within relatively close proximity to the location at which the medical device will be used in a medical procedure (e.g., within an operating room, etc.). While several systems and methods have been made and used to charge or recharge power sources, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
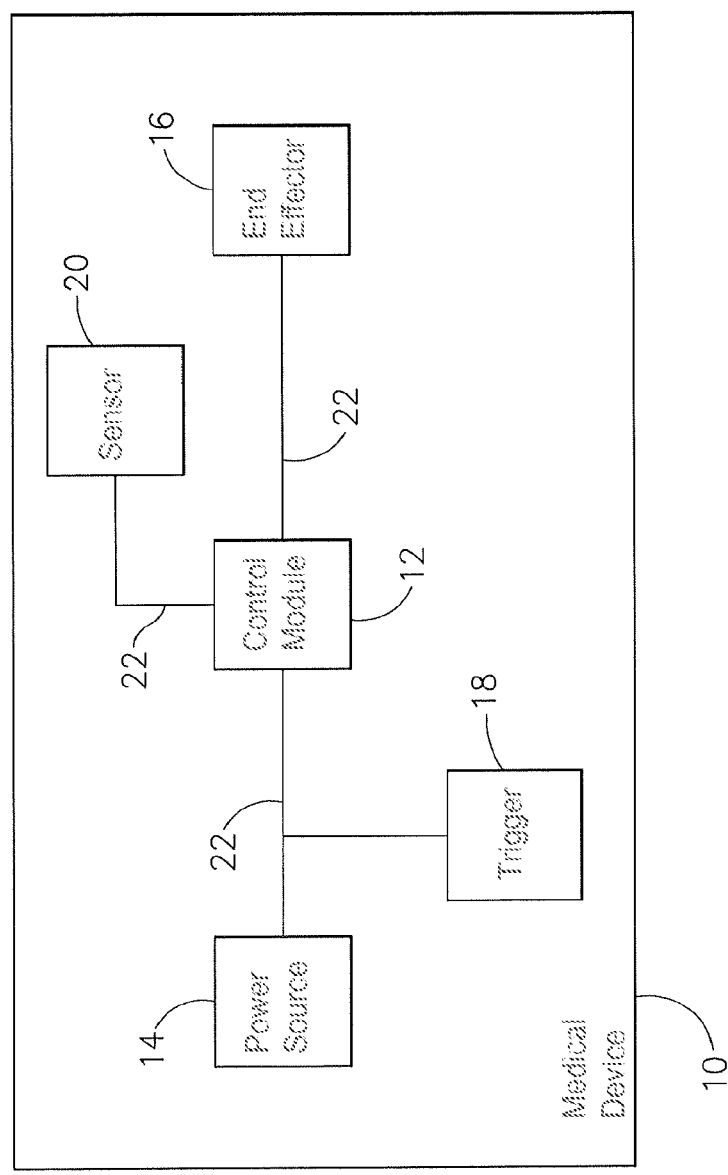
FIG. 1 depicts a schematic view of an exemplary medical device having an internal power source.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various, accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

I. Medical Devices for Use with Insertable or Reclaimable Components

FIG. 1 shows components of an exemplary medical device (10) in diagrammatic block form. As shown, medical device (10) comprises a control module (12), a power source (14), and an end effector (16). Merely exemplary power sources (14) may include NiMH batteries, Li-ion batteries (e.g., prismatic cell type lithium ion batteries, etc.), Ni-Cad batteries, or any other type of power source as may be apparent to one of ordinary skill in the art in light of the teachings herein. Control module (12) may comprise a microprocessor, an application specific integrated circuit (ASIC), memory, a printed circuit board (PCB), a storage device (such as a solid state drive or hard disk), firmware, software, or any other suitable control module components as will be apparent to one of ordinary skill in the art in light of the teachings herein. Control module (12) and power source (14) are coupled by an electrical connection (22), such as a cable and/or traces in a circuit board, etc., to transfer power from power source (14) to control module (12). Alternatively, power source (14) may be selectively coupled to control module (12). This allows power source (14) to be detached and removed from medical device (10), which may further allow power source (14) to be readily recharged or reclaimed for resterilization and reuse, such as in accordance with the various teachings herein. In addition or in the alternative, control module (12) may be removed for servicing, testing, replacement, or any other purpose as will be apparent to one of ordinary skill in the art in view of the teachings herein.

End effector (16) is coupled to control module (12) by another electrical connection (22). End effector (16) is configured to perform a desired function of medical device (10). By way of example only, such function may include cauterizing tissue, ablating tissue, severing tissue, ultrasonically vibrating, stapling tissue, or any other desired task for medical device (10). End effector (16) may thus include an active feature such as an ultrasonic blade, a pair of clamping jaws, a sharp knife, a staple driving assembly, a monopolar RF electrode, a pair of bipolar RF electrodes, a thermal heating element, and/or various other components. End effector (16) may also be removable from medical device (10) for servicing, testing, replacement, or any other purpose as will be apparent to one of ordinary skill in the art in view of the teachings herein. In some versions, end effector (16) is modular such that medical device (10) may be used with different kinds of end effectors (e.g., as taught in U.S. Provisional Application Ser. No. 61/410,603, etc.). Various other configurations of end effector (16) may be provided for a variety of different functions depending upon the purpose of medical device (10) as will be apparent to those of ordinary skill in the art in view of the teachings herein. Similarly, other types of components of a medical device (10) that may receive power from power source (14) will be apparent to those of ordinary skill in the art in view of the teachings herein.

Medical device (10) of the present example includes a trigger (18) and a sensor (20), though it should be understood that such components are merely optional. Trigger (18) is coupled to control module (12) and power source (14) by electrical connection (22). Trigger (18) may be configured to selectively provide power from power source (14) to end effector (16) (and/or to some other component of medical device (10)) to activate medical device (10) when performing a procedure. Sensor (20) is also coupled to control module (12) by an electrical connection (22) and may be configured to provide a variety of information to control module (12) during a procedure. By way of example only, such configurations may include sensing a temperature at end effector (16) or determining the oscillation rate of end effector (16). Data from sensor (20) may be processed by control module (12) to effect the delivery of power to end effector (16) (e.g., in a feedback loop, etc.). Various other configurations of sensor (20) may be provided depending upon the purpose of medical device (10) as will be apparent to those of ordinary skill in the art in view of the teachings herein. Of course, as with other components described herein, medical device (10) may have more than one sensor (20), or sensor (20) may simply be omitted if desired.

Figure 2:
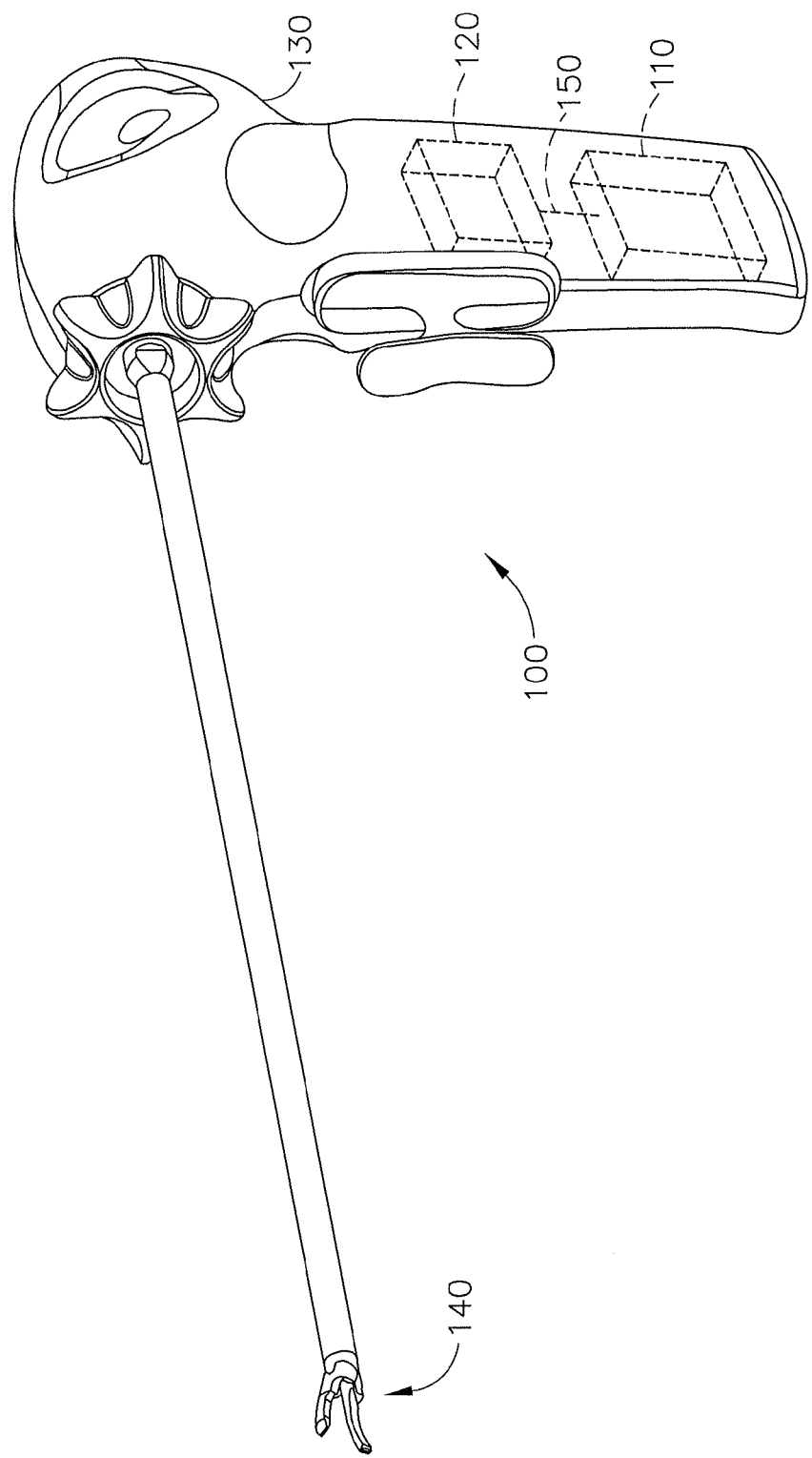
FIG. 2 depicts a perspective view of an exemplary medical device having an internal power source.

FIG. 2 depicts a merely exemplary form that medical device (10) may take. In particular, FIG. 2 shows a medical device and/or surgical instrument (100) comprising a power source (110), a control module (120), a housing (130), end effector (140), and an electrical connection (150). In the present example, power source (110) is located internally within housing (130) of surgical instrument (100). Alternatively, power source (110) may only partially extend into housing (130) and may be selectively attachable to a portion of housing (130). In yet a further exemplary configuration, a portion of housing (130) may extend into power source (110) and power source (110) may be selectively attachable to the portion of housing (130). Power source (110) may also be configured to detach from surgical instrument (100) and decouple from control module (120) or electrical connection (150). As a result, power source (110) may be completely separated from surgical instrument (100) in some versions. As is readily apparent, this may allow the power source (110) to be removed to be recharged or reclaimed for resterilization and reuse, such as in accordance with various teachings herein. After recharging, or after an initial charge, power source (110) may be inserted or reinserted into surgical instrument (100) and secured to housing (130) or internally within housing (130). Of course, surgical instrument (100) may also allow power source (110) to be charged and/or recharged while power source (110) is still in or otherwise coupled relative to housing (130).

It should also be understood that control module (120) may be removed for servicing, testing, replacement, or any other purpose as will be apparent to one of ordinary skill in the art in view of the teachings herein. Further, end effector (140) may also be removable from surgical instrument (100) for servicing, testing, replacement, or any other purpose as will be apparent to one of ordinary skill in the art in view of the teachings herein. While certain configurations of an exemplary surgical instrument (100) have been described, various other ways in which surgical instrument (100) may be configured will be apparent to those of ordinary skill in the art in view of the teachings herein. By way of example only, medical devices and/or surgical instruments (10, 100) and/or any other medical device referred to herein may be constructed in accordance with at least some of the teachings of U.S. Pat. No. 6,500,176; U.S. Pat. No. 6,783,524; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pat. No. 7,416,101; U.S. Pat. No. 7,738,971; U.S. Pub. No. 2006/0079874; U.S. Pub. No. 2007/0191713; U.S. Pub. No. 2007/0282333; U.S. Pub. No. 2008/0200940; U.S. Pub. No. 2009/0143797, now U.S Pat. No. 8,419,757, issued Apr. 16, 2013; U.S. Pub. No. 2009/0209990, now U.S. Pat. No. 8,657,174, issued Feb. 25, 2014; U.S. Pub. No. 2010/0069940, now U.S. Pat. No. 9,023,071, issued May 5, 2015; U.S. Pub. No. 2011/0015660, now U.S. Pat. No. 8,461,744, issued Jun. 11, 2013; U.S. Pat. Pub. No. 2011/0087218, now U.S. Pat. No. 8,939,974, issued Jan. 27, 2015; U.S. patent application Ser. No. 13/151,481, now U.S. Pat. No. 9,161,803; and/or U.S. Provisional Application Ser. No. 61/410,603. The disclosures of each of those documents are incorporated by reference herein in their entirety.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

II. Exemplary Charging Station

It will be appreciated that during the course of using surgical instrument (100), some parts of surgical instrument may be disposable while other parts may be reused. In some instances, it will be appreciated that for reusable components it may be desirable to have a place to store the reusable components. To the extent that any reusable components may require charging, it may be desirable that the area used for storage of a reusable component may also be used for recharging any components that may need to be recharged, such as any rechargeable batteries, as will be discussed in further detail below.

Figure 3:
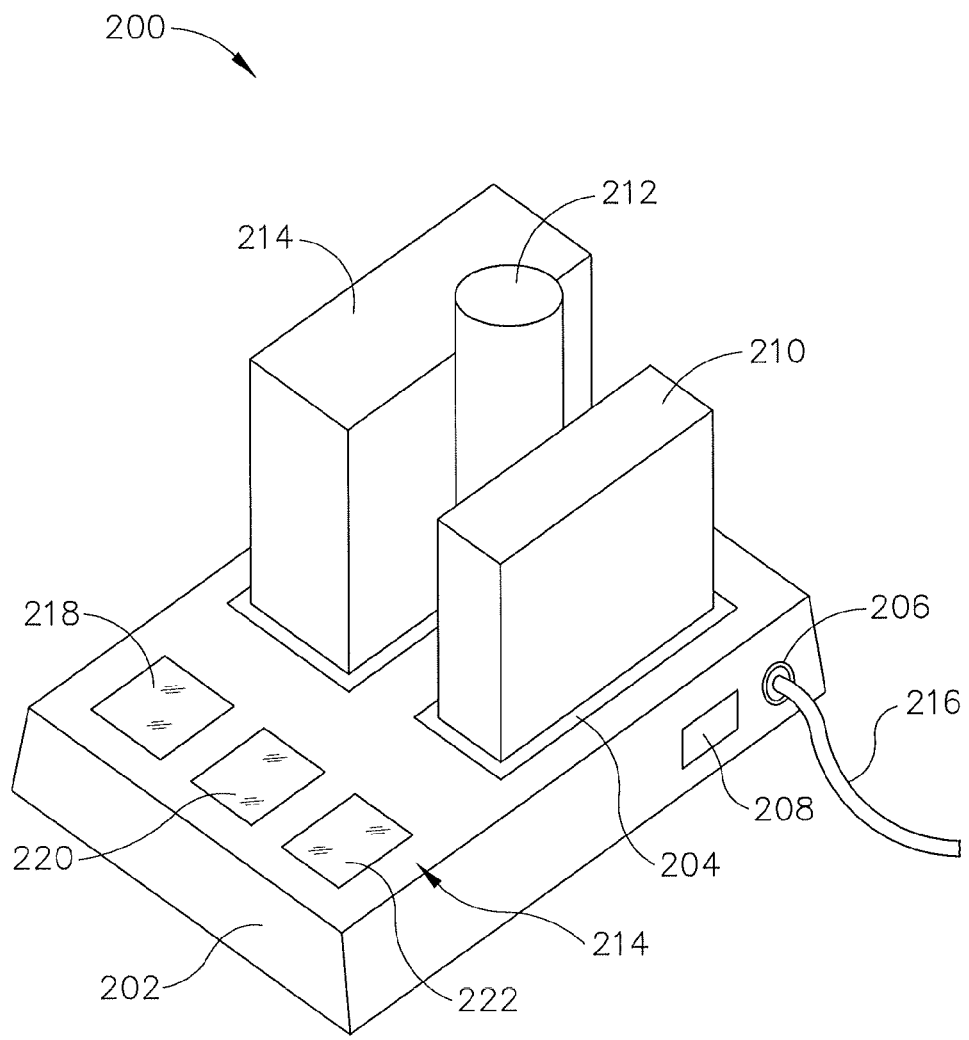
FIG. 3 depicts a perspective view of an exemplary charging station.

FIG. 3 shows an exemplary charging station (200) having a base (202) with at least one charging slot (204) shaped to receive various components of instrument (100). Base (202) in the present example has a flat, rectangular shape, though any other shape may be used. Slots (204) may hold, for example, a rechargeable battery (210), an ultrasonic transducer (212), or a reusable electronics module (214). In some exemplary versions, transducer (212) may be screwed into slot (204) to establish communication with base (202). Slots (204) are shaped to provide a seat for components held in slots (204). In some versions, slots (204) may be slightly bigger than the shape of the components being held by slots (204) or may have a slightly tapered edge to provide for easy insertion into slots (204).

Furthermore, in some exemplary versions, slots (204) may comprise a light or other indicator integrated into slots (204) operable to light up, flash, or otherwise provide a signal to the user until the user places the appropriate reusable component into slot (204). Therefore, it will be understood that slots (204) with an indictor integrated into slots (204) may be used to help ensure that reusable components are not inadvertently disposed of after a surgical procedure. In the present example, base (202) comprises a number of slots (204) equal to the number of reusable components of surgical instrument (100). As a result, if one of the reusable components, such as battery (210), is missing, then the empty slot can visually indicate to the user that a reusable component is missing. Thereafter, the user may look for and replace the missing component.

Base (202) may further comprise power port (206) and a data port (208). Power port (206) is in communication with a power cord (216), which is connected to a wall outlet or other external power source such that power port (206) may draw power to power base (202), which may be used to power various indicator functions as will be described below or may be used to recharge components plugged into base (202). In some other exemplary versions, battery (210), which may have unused charge, may be used to power base (202). In yet some other exemplary versions, battery (210) may be used to provide power to base (202) until all components are placed into base (202), in which thereafter power is drawn from an external power source through power port (206) rather than through battery (210). In some other versions, a combination of power drawn from battery (210) and an external power source may be used for powering base (202). Other suitable ways of powering base (202) will be apparent to one of ordinary skill in the art in view of the teachings herein.

Data port (208) may be connected to a computer or any other external device for analysis of power usage and/or states of components plugged into base (202). It will be appreciated that other suitable uses for data port may be used as would be apparent to one of ordinary skill in the art in view of the teachings herein.

Furthermore, base (202) may comprise at least one indicator light (214) operable to inform the user of various states and statuses of base (202) as well as statuses regarding the components plugged into base (202). In the present example, base (202) comprises a battery indicator (218), a transducer indicator (220) and an electronic package status indicator (222), which are operable to provide status information to the user regarding battery (210), transducer (212), and electronics (214), respectively. For example, information regarding whether the respective component is plugged in may be provided. In some exemplary versions, information may be provided to the user regarding whether the respective component is ready to be used. Any other suitable information may be provided through use of battery indicator (218), transducer indicator (220), and electronics indicator (222). For example, battery indicator (218) may be used to inform the user of a charge level for battery (210) and a timer to inform the user of when battery (210) will be fully charged. Transducer indicator (220) may be used to inform the user whether transducer (212) is ready for use. Electronics indicator (222) may be used to inform the user of whether electronics (214) are properly functioning.

It will be appreciated that any of electronics indicator (222), battery indicator (218), and/or indicator light (214) may comprise an LCD or other suitable visual output device operable to provide textual and/or otherwise visual information to the user regarding the status of the various components. Furthermore, any failures or errors that occur regarding electronics indicator (222), battery indicator (218), indicator light (214), and/or components in communication with or monitored by the aforementioned components, may be communicated to the user by outputting a message and/or diagnostic information. A display may also provide troubleshooting messages and/or suggestions of remedial steps that may be taken. It will also be appreciated that rather than having three separate indicators or displays, any other suitable configurations may be used as will be apparent to one of ordinary skill in the art in view of the teachings herein. For example, a single LCD or other suitable display may be operable as electronics indicator (222), battery indicator (218), and/or indicator light (214).

Base (202) may further be used to sterilize the components held on base (202) by placing base (202) into a sterilizer for sterilization of base (202). In some versions, the sterilizer may comprise an autoclave, but any suitable sterilization device and/or method may be used as would be apparent to one of ordinary skill in the art in view of the teachings herein. For example, gas plasma, ethylene oxide, or any other suitable sterilization method may be used. In other exemplary versions, base (202) may be used to hold components for sterilization using any suitable method as would be apparent to one of ordinary skill in the art in view of the teachings herein.

In some exemplary versions, a mat rather than slots (204) may be used to hold components for charging and/or sterilization. It will be appreciated that the mat may be integrated into a table or alternatively be incorporated and held as part of a robotic arm. In yet other exemplary versions, the mat or slots (204) may be operable to wirelessly charge battery (210) through induction. Furthermore, wireless communication may be used to establish communication with any components placed on base (202).

III. Exemplary Counters

Figure 4:
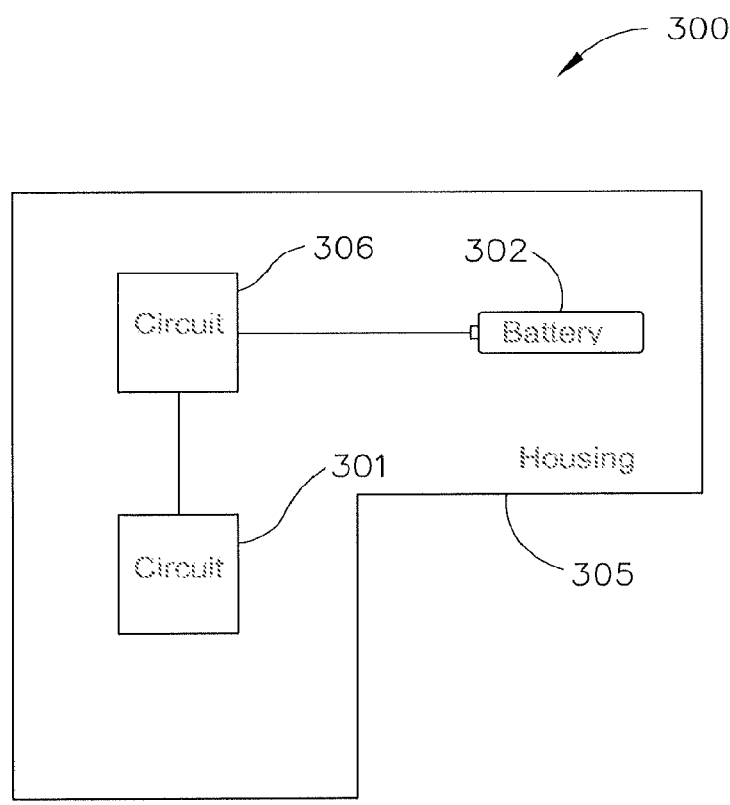
FIG. 4 depicts a block diagram view of an exemplary battery pack.

FIG. 4 shows an exemplary battery pack (300) that may be used in conjunction with, for example, base (202) of FIG. 3. Battery pack (300) comprises a housing (305), a battery (302), a microprocessor circuit with non-volatile memory (301), and a coulomb counting circuit (306). Microprocessor circuit (301) is in communication with coulomb counting circuit (306). Coulomb counting circuit (306) is operable to provide for accurate monitoring of charge states of battery (302). Coulomb counting circuit (306) may be operable to recharge battery (302).

Microprocessor circuit (301) is operable to keep the charge state date updated such that it keeps track of when charge state has gone from empty to full and/or vice versa. Microprocessor circuit (301) is also operable to demodulate and recover data received from a charger such as base (202) of FIG. 3 and/or coulomb counting circuit (306). Microprocessor circuit (301) is further operable to transmit commands to increase, decrease, turn off, or maintain the current rate of charging to coulomb counting circuit (306) as coulomb counting circuit (306) charges battery (302), therefore forming a closed feedback loop for charging battery (302).

In some exemplary versions, when battery (302) is initially fully charged, a cycle counter contained within microprocessor circuit (301) is reset to zero. Microprocessor circuit (301) may also contain an empirical model based on battery's (302) behavior with respect to charge cycles over time such as number of charge cycles, temperature of battery (302), number of charge cycles at various temperatures, and/or battery's (302) ability to hold charge over time. As a result, behavior of battery (302) may be more predictable, resulting in accurate charges to battery (302) as well as accurate reporting regarding battery's (302) status. Microprocessor circuit (301) may be programmed to periodically monitor battery (302) as battery (302) undergoes various temperatures, sterilization procedures, or any other suitable readings as would be apparent to one of ordinary skill in the art in view of the teachings herein. As a result, it will be understood that having more information regarding battery (302) will enable microprocessor circuit (301) to provide more accurate estimates for charge remaining in battery (302). Furthermore, it will be appreciated that periodically, battery (302) may be fully charged and fully discharged. The information from a full recharge and discharge cycle may be provided to microprocessor circuit (301), thereby enabling microprocessor circuit (301) to provide a more accurate estimate regarding remaining charge of battery (302). By way of example only, microprocessor circuit (301) may demodulate and recover data from a charger (e.g., data contained in a carrier superimposed on the charging waveform) and transmit data to the charger to command it to increase, decrease, turn off, or maintain the current rate of charge, thus enabling a closed loop feedback control mechanism for charging.

It will be appreciated that in some exemplary versions, microprocessor circuit (301) may be in communication with an Ethernet port or modem such that microprocessor circuit (301) can communicate charge cycle information across a network. By communicating charge cycle information across a network, battery pack (300) may be integrated into a system where use of battery pack (300) is billed on a per-charge-cycle or otherwise suitable basis.

In addition to battery cycles, it will be appreciated that it may be desirable to monitor the number of battery connects and disconnects. It will be appreciated that a counter for determining the number of battery connections may be used as is taught, for example in U.S. Pat. No. 7,464,846, titled "Surgical Instrument Having a Removable Battery," issued on Dec. 16, 2008, the disclosure of which is incorporated by reference herein. As a result, it will be understood that through careful monitoring of battery charge cycles and the number of connections made by battery (302), more accurate information about battery may result.

Furthermore, in some exemplary versions, battery (302) may be charged prior to shipping and battery (302) may be operable to have data stored within battery (302) such as its fully charged status and/or a counter indicative of the number of charge cycles that battery (302) has undergone. Such information may be stored, for example, on a chip integrated with battery (302). Battery (302) may be operable to develop and store an empirical model of battery (302) behavior in relation to battery's (302) age, charge state as battery (302) ages, aging of battery (302) in relation to calendar time, temperature of battery (302), and total number of recharge cycles of battery (302). It will be appreciated that the chip of battery (302) may be programmed to periodically "wake up" and monitor characteristics of battery (302) such as temperature, autoclave sterilization cycles, and charge states. Furthermore, any recorded information regarding battery (302) may be used to update battery (302) related models to more accurately predict battery (302) discharge time. It will further be appreciated that battery (302) may be measured/monitored to determine the true charge capacity of battery (302) on a yearly basis, quarterly basis, bi-annually, or in any other suitable time frame.

IV. Exemplary Modular Electronics Unit

In some instances, it may be desirable during and between uses of surgical instrument (100) as shown in FIG. 2 to house the electrical components separately from the mechanical components. One exemplary reason for doing so is that electrical components may require separate sterilization and charging. However, it will be understood that there may be a variety of other reasons for separating electrical components from mechanical components.

Figure 5:
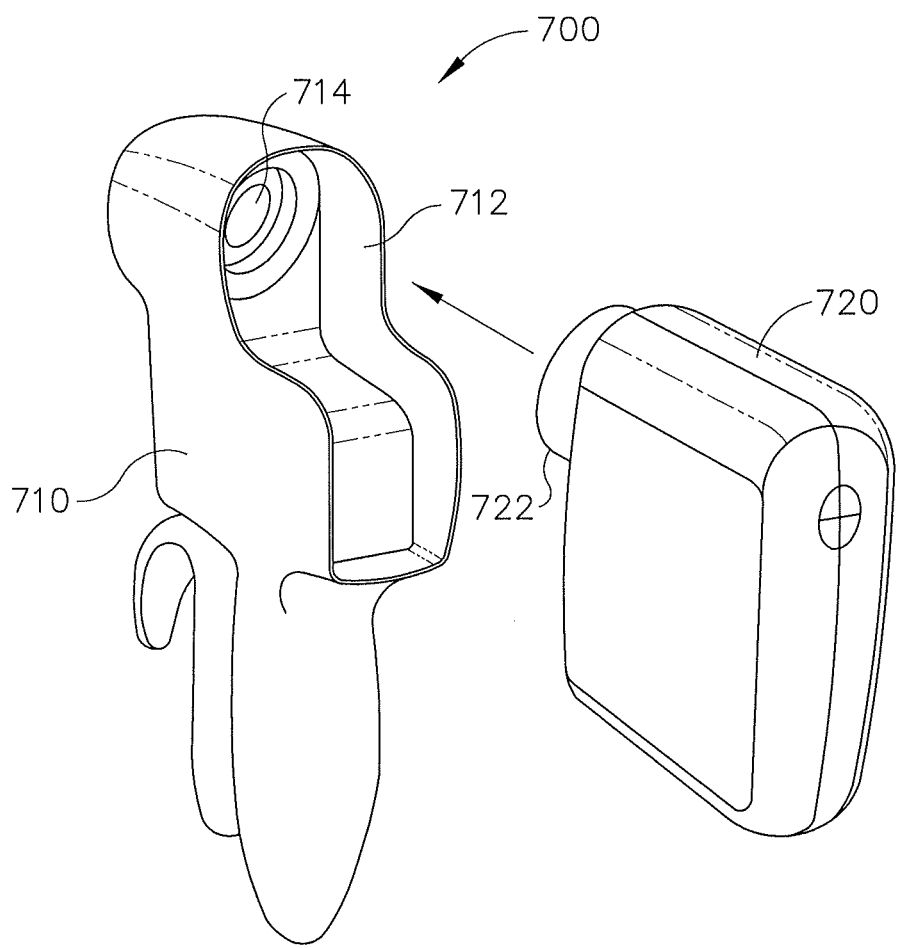
FIG. 5 depicts a perspective view of an exemplary alternative version of a handle assembly.
Figure 6:
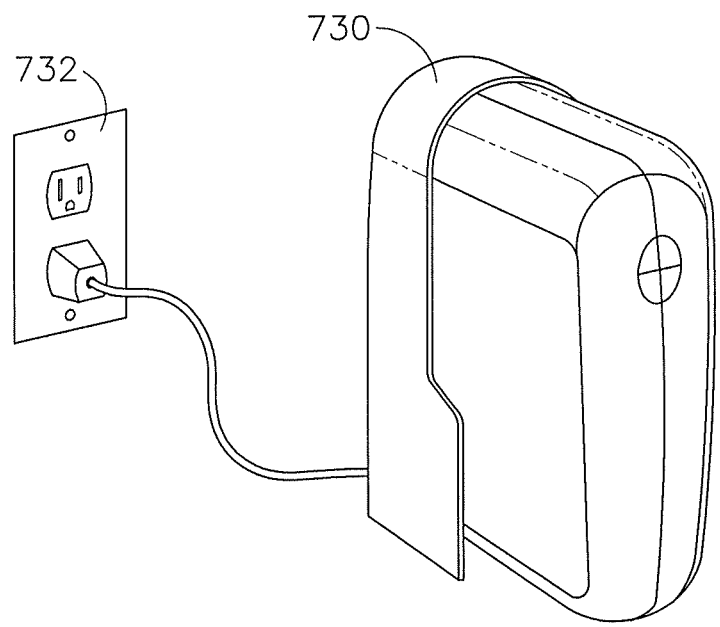
FIG. 6 depicts a perspective view of an exemplary electrical module of FIG. 5.
Figure 7:
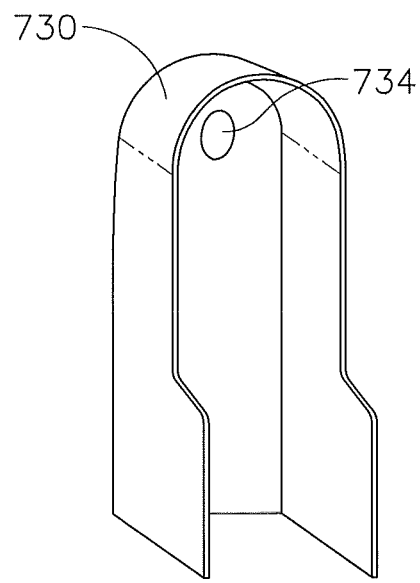
FIG. 7 depicts a perspective view of an exemplary charging socket of FIG. 6.

FIGS. 5-7 show an exemplary handle assembly (700) having a mechanical module (710) and an electrical module (720). It will be appreciated that surgical instrument (100) of FIG. 2 may be adapted to have such a configuration. All of the electrical components of an exemplary surgical instrument may be contained within electrical module (720). Mechanical module (710) comprises a receiving socket (712) and a connection port (714) positioned within receiving socket (712). Electrical module (720) is shaped to complement receiving socket (712) such that electrical module (720) can be placed within receiving socket (712). Electrical module (720) comprises a connector plug (722) operable to couple with connection port (714) to enable electrical module (720) to establish electrical communication with handle assembly (700) through the use of, for example, metal contacts, or any other suitable means for establishing a connection as would be apparent to one of ordinary skill in the art in view of the teachings herein.

Once removed from handle assembly (700), electrical module (720) may be connected to a charging socket (730), which may be plugged into a wall outlet (732). Connector plug (722) may be inserted into a charging port (734) to receive power from wall outlet (732). It will further be appreciated that electrical module (720) may be hermetically sealed such that only the outer surface of electrical module (720) may need to be sterilized prior to using electrical module (720) with handle assembly (700). Accordingly, the user may remove electrical module (720) from handle assembly (700) after use such that electrical module (720) may then be sterilized. In some exemplary versions, electrical module (720) may be insulated from heat such that steam sterilization may be used to sterilize electrical module. After surgical procedures, it will be appreciated that mechanical module (710) may be disposed of or reclaimed to repeat use. It will be appreciated that electrical module (720) may be reused through sterilization of electrical module (720). In some versions, electronics module (720) may be insertable into a sealed housing (not shown) within handle assembly (700). Aseptic techniques could be used to place electronics module (720) in the sealed housing. The sealed housing may form a hermetic seal for holding electronics module (720), such that the sealed electronics module (720) is not exposed to the surgical field during use of the instrument, and such that the sealed electronics module (720) need not be sterilized after/between uses of the surgical instrument.

V. Exemplary Battery and Battery Control

Figure 8:
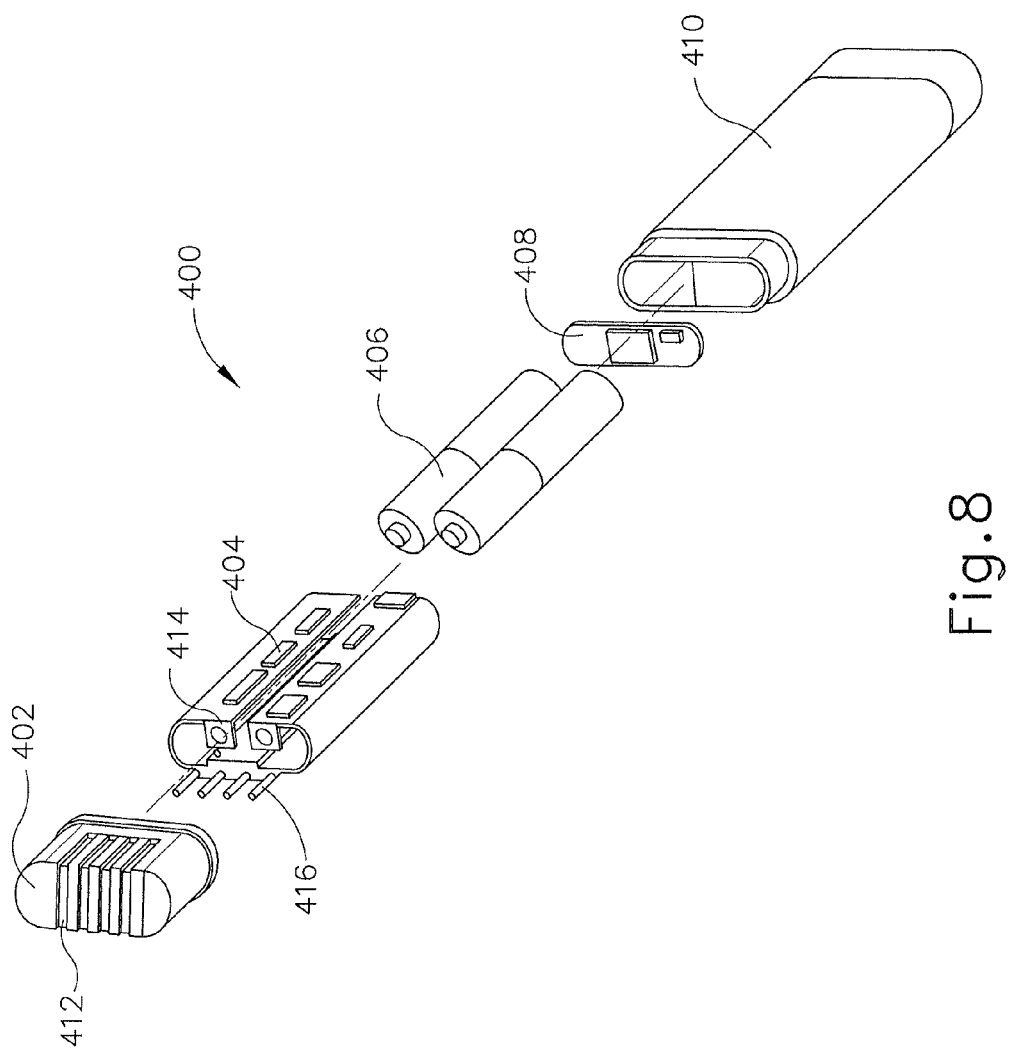
FIG. 8 depicts a perspective, exploded view of an exemplary alternative battery pack.

It will be appreciated that a variety of batteries may be used with surgical instrument (100) as shown in FIG. 2. FIG. 8 depicts an integrated battery pack (400), which may be used with, for example surgical instrument (100). Pack (400) comprises a cap (402), flex circuit (404), batteries (406), radio board (408), and outer body (410).

Cap (402) comprises metal inserts (412) operable to provide contacts to establish electrical communication with surgical instrument (100). Metal inserts (412) are in communication with batteries (406) such that pack (400) is operable to deliver power from batteries (406) to a surgical instrument (100) such as shown in FIG. 2. Metal inserts (412) are operable provide a connection regardless of the orientation of pack (400) when inserted into surgical instrument (100).

Flex circuit (404) is shaped to wrap around batteries (406) and establish communication between batteries (406) and cap (402). Flex circuit (404) includes battery contacts (414) and cap contacts (416). Battery contacts (414) are operable to establish electrical communication with batteries (406) whereas cap contacts (416) are operable to establish electrical communication with metal inserts (412) of cap (402). Flex circuit (404) further comprises circuitry operable to manage power delivered from batteries (406). For example, surgical instrument (100) may have different requirements regarding voltage or current levels. Flex circuit (404) may comprise circuitry operable for use with different types of surgical instruments (100) (e.g., ultrasonic surgical instruments and RF electrosurgical instruments, etc.). For example, circuitry may be used that is universally compatible with different types of surgical instruments or in the alternative, flex circuit (404) may comprise several different pieces of circuitry to be separately compatible with different types of surgical instruments. Flex circuit (404) may also be operable to determine the type of surgical instrument that pack (400) is connected to such that flex circuit (404) may be operable to adjust the power delivery from pack (400) to suit the power needs of the instrument connected to pack (400). Furthermore, flex circuit (404) is operable to track and store the power usage of the instrument in communication with pack (400). Flex circuit (404) may also comprise a power port such that flex circuit (404) may be connected to an external power source to charge batteries (406). It will also be understood that since flex circuit (404) is operable to control the power deliver of batteries (406), the surgical instrument ultimately need not contain any circuitry regarding power management as flex circuit (404) is operable to handle power management for the surgical instrument. As pack (400) is reused with, for example, a different type of surgical instrument, flex circuit (404) may actively change the delivery of power provided to the surgical instrument. Flex circuit (404) may be configured to have a digital handshake with various surgical instruments to determine the type of surgical instruments connected to flex circuit (404).

Batteries (406) in the present example comprise a cluster of batteries shrink wrapped together. In some exemplary versions, batteries (406) may be shrink wrapped together using a biodegradable plastic. Of course, any other suitable type of wrap may be used; or wrap may be omitted. The shrink wrap may later be removed during battery (406) reprocessing. Batteries (406) may comprise lithium polymer batteries, one or more super capacitors, nickel cadmium, lithium ion, nickel metal-hydride, or any other suitable types of batteries as would be apparent to one of ordinary skill in the art in view of the teachings herein.

Batteries (406) are further in communication with radio board (408). Radio board (408) comprises a wireless connection module such as a WiFi and/or Bluetooth module operable to communicate with an external display device. In the present example, radio board (408) is seated at the bottom of outer body (410) sealed in a radio transparent material such that radio board (408) is fully able to communicate wirelessly within outer body (410). It will be understood that in the present example, radio board (408) need not necessarily be used if the user determines that communication to an external display device is not necessary.

Outer body (410) is operable to hold batteries (406) radio board (408), and flex circuit (404). Cap (402) has a shape operable to cover outer body (410) thereby enclosing all of the components held in outer body (410). It will be appreciated that outer body (410) and cap (402) are operable to form a hermetic and/or fluid tight seal. Outer body (410) may comprise magnesium and/or a shield specific plastic operable to protect contents contained therein. Since outer body (410) is operable to protect components, batteries (406) and/or other electronics and components contained within outer body (410) may be reused multiple times and may be cleaned prior to reuse.

VI. Exemplary Pull Tabs

Figure 9:
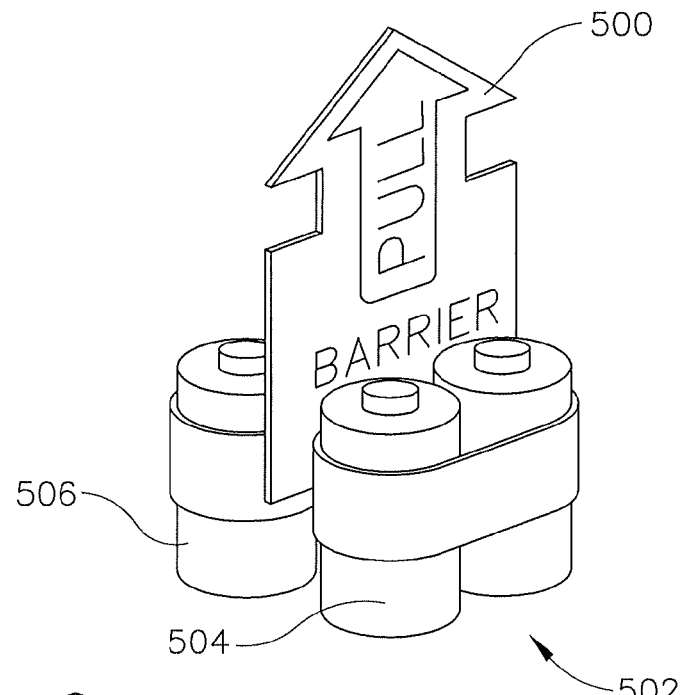
FIG. 9 depicts a perspective view of an exemplary version of batteries having a pull tab.
Figure 10:
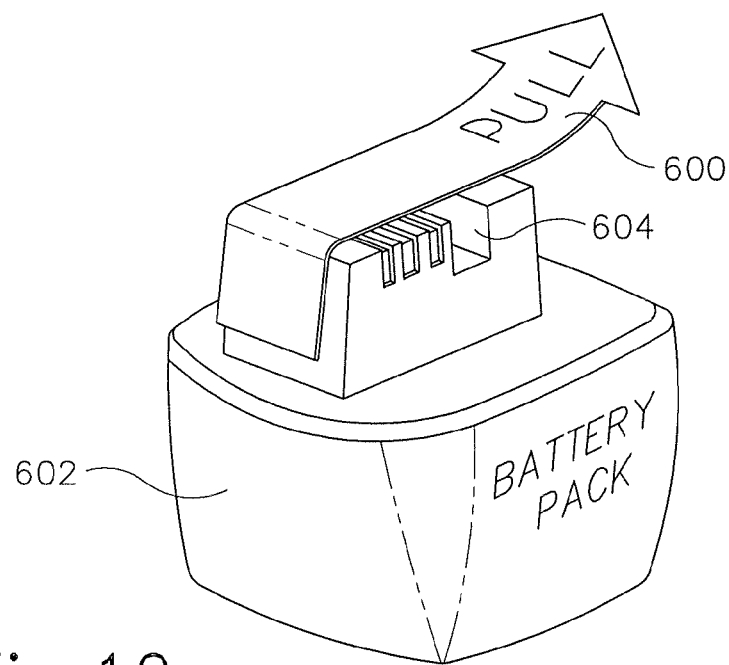
FIG. 10 depicts a perspective view of an exemplary battery pack having a pull tab.

FIGS. 9-10 show an exemplary pull tab (500, 600) for use with batteries (502) and/or a battery pack (602). It will be understood that shipping restrictions with respect to certain kinds of batteries such as, for example, lithium ion or lithium polymer batteries may require that batteries (502) be isolated during shipment and/or prior to use. FIG. 9 shows pull tab (500) isolating a first pair of batteries (504) from a second pair of batteries (506). FIG. 10 shows a pull tab (600) covering a contact (604) of battery pack (602). It will be appreciated that contact (604) may need to be isolated during shipping of battery pack (602), thus exemplary pull tab (600) may be used. In either version, when batteries (502) or battery pack (602) is ready for use, pull tab (500, 600) may be removed by the user and batteries (502) or battery pack (602) may be used with a surgical instrument (100), such as the one shown in FIG. 2.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a base comprising a housing and at least one engagement means, wherein the at least one engagement means is shaped to receive at least one reusable component from a surgical instrument, wherein the at least one reusable component comprises at least a first energy means and a second energy means, wherein the first energy means and the second energy means are operable to provide for separate functions of the surgical instrument, wherein the at least one engagement means is operable to alert a user in response to an absence of the first energy means or the second energy means from the at least one engagement means; and (b) at least one indicator in communication with the base, wherein the at least one indicator is in further communication with the at least one engagement means, wherein the base is configured to detect at least one characteristic operatively associated with the at least one reusable component placed into the at least one engagement means, wherein the at least one indicator is configured to provide a signal to a user regarding the at least one characteristic.

2. The apparatus of claim 1, wherein the first energy means comprises a battery, wherein the at least one characteristic comprises a charge level for the battery.

3. The apparatus of claim 1, wherein the second energy means comprises an ultrasonic transducer, wherein the at least one characteristic comprises a status for the ultrasonic transducer.

4. The apparatus of claim 1, wherein the second energy means comprises an electronics module, wherein the at least one characteristic comprises a status for the electronics module.

5. The apparatus of claim 4, wherein the electronics module is hermetically sealed and removable from the surgical instrument.

6. The apparatus of claim 5, wherein the surgical instrument further comprises a mechanical module.

7. The apparatus of claim 2, wherein the base comprises a coulomb counter to measure the charge of a battery insertable into the base.

8. The apparatus of claim 1, wherein the number of the at least one engagement means equals the number of the at least one reusable components.

9. The apparatus of claim 1, wherein the base is insertable into a sterilizer.

10. The apparatus of claim 1, wherein at least a portion of the base is shrink wrapped with a biodegradable plastic.

11. The apparatus of claim 2, further comprising a battery pack insertable into the at least one engagement means, wherein the battery pack is operable to hold a plurality of batteries.

12. The apparatus of claim 11, wherein the battery pack further comprises a pull tab in communication with the battery pack.

13. The apparatus of claim 1, wherein the base has a mat shape operable to receive the at least one reusable component.

14. The apparatus of claim 1, wherein the base is in selective wireless communication with the at least one reusable component.

15. An apparatus comprising:
(a) a surgical instrument having a battery and an ultrasonic transducer, wherein the battery and the ultrasonic transducer are removable together as a unit from the surgical instrument, wherein the battery comprises a rechargeable battery;
(b) a base, wherein the base comprises at least one engagement means operable to receive the rechargeable battery and the ultrasonic transducer, wherein the base comprises at least one visual indicator in communication with the at least one engagement means, wherein the base is configured to monitor at least one aspect of the battery or the ultrasonic transducer, wherein the base is further configured to monitor at least one aspect of the surgical instrument, wherein the base further comprises an indicator operable to alert a user in response to an absence of the rechargeable battery or the ultrasonic transducer from the base; and
(c) a charging module in communication with the base, wherein the charging module is configured to charge the rechargeable battery, wherein the charging module is in communication with the at least one visual indicator.

16. The apparatus of claim 15, wherein the charging module is operable to monitor the charge level of the battery, wherein the charging module is configured to monitor the number of charge cycles undergone by the battery.

17. The apparatus of claim 15, wherein the charging module is operable to indicate to the user the charge status of the battery.

18. The apparatus of claim 15, wherein the rechargeable battery is contained within an electronics module, wherein the electronics module is operable to be removed from the surgical instrument, wherein the electronics module is configured to be in selective communication with a wall adapter, wherein the electronics module is operable to charge the rechargeable battery through the wall adapter.

19. A method of monitoring the status of a plurality of components for use with a surgical instrument by using a base configured to receive the plurality of components, wherein the plurality of components are configured to be reusable components, wherein the plurality of components comprises at least a first energy means and a second energy means, wherein the first energy means and the second energy means are operable to provide for separate functions of the surgical instrument, the method comprising:
(a) using the surgical instrument;
(b) removing the first energy means and the second energy means from the surgical instrument;
(c) placing one or both of the first energy means and the second energy means into the base;
(d) alerting the user in response to an absence of the first energy means or the second energy means from the base;
(e) verifying that the first energy means and the second energy means have been inserted into the base; and
(f) providing status information regarding first energy means and the second energy means.

* * * * *